(12) United States Patent
Clarke et al.

(10) Patent No.: US 12,151,086 B2
(45) Date of Patent: *Nov. 26, 2024

(54) INJECTION DEVICE

(71) Applicant: Norton Healthcare Limited, Castleford (GB)

(72) Inventors: Christopher John Clarke, Walton on Thames (GB); Joseph Peter Corrigan, Cambridge (GB)

(73) Assignee: Norton Healthcare Limited, Castleford (GB)

( * ) Notice: Subject to any disclaimer, the term of this patent is extended or adjusted under 35 U.S.C. 154(b) by 166 days.

This patent is subject to a terminal disclaimer.

(21) Appl. No.: 17/897,199

(22) Filed: Aug. 28, 2022

(65) Prior Publication Data

US 2022/0401653 A1 Dec. 22, 2022

Related U.S. Application Data

(63) Continuation of application No. 16/580,075, filed on Sep. 24, 2019, now Pat. No. 11,433,185.

(30) Foreign Application Priority Data

Sep. 24, 2018 (GB) ..................................... 1815552

(51) Int. Cl.
*A61M 5/315* (2006.01)
*A61M 5/32* (2006.01)
*A61M 5/50* (2006.01)

(52) U.S. Cl.
CPC .... *A61M 5/31511* (2013.01); *A61M 5/31505* (2013.01); *A61M 5/3158* (2013.01); *A61M 5/3202* (2013.01); *A61M 5/5013* (2013.01); *A61M 5/5066* (2013.01); *A61M 5/3157* (2013.01); *A61M 5/3205* (2013.01); *A61M 2205/3317* (2013.01); *A61M 2205/3576* (2013.01); *A61M 2205/581* (2013.01); *A61M 2205/582* (2013.01); *A61M 2205/587* (2013.01)

(58) Field of Classification Search
CPC .......... A61M 5/31505; A61M 5/31511; A61M 5/5066

See application file for complete search history.

(56) References Cited

U.S. PATENT DOCUMENTS

| | | |
|---|---|---|
| 4,252,118 A | 2/1981 | Richard |
| 4,391,272 A | 7/1983 | Staempfli |

(Continued)

FOREIGN PATENT DOCUMENTS

| | | |
|---|---|---|
| EP | 0442260 A1 | 8/1991 |
| EP | 1702634 A1 | 9/2006 |

(Continued)

*Primary Examiner* — Bradley J Osinski
(74) *Attorney, Agent, or Firm* — Blank Rome LLP

(57) ABSTRACT

An injection device is described. The injection device includes a stopper having a first conductive element, a barrel having a medicament reservoir sealed at a proximal end with the stopper, and a plunger rod having a second conductive element. The plunger rod is coupled with the stopper to cause forward axial movement of the stopper to expel a medicament from the medicament reservoir. The first conductive element and the second conductive element complete an electrical circuit when the plunger rod is coupled to the stopper.

30 Claims, 10 Drawing Sheets

(56) References Cited

U.S. PATENT DOCUMENTS

| | | | |
|---|---|---|---|
| 4,923,443 A | 5/1990 | Greenwood | |
| 4,950,243 A | 8/1990 | Estruch | |
| 5,032,114 A | 7/1991 | Olovson | |
| 5,059,179 A | 10/1991 | Quatrochi | |
| 5,078,686 A | 1/1992 | Bates | |
| 5,084,017 A | 1/1992 | Maffetone | |
| 5,125,899 A | 6/1992 | Frignoli | |
| 5,562,623 A | 10/1996 | Shonfeld | |
| 6,129,712 A | 10/2000 | Sudo | |
| 2005/0080384 A1* | 4/2005 | Green | A61M 5/31511 604/218 |
| 2016/0030683 A1* | 2/2016 | Taylor | A61M 5/345 604/151 |
| 2016/0259913 A1 | 9/2016 | Yu | |
| 2017/0165423 A1 | 6/2017 | Holland | |
| 2017/0312430 A1 | 11/2017 | Schleicher | |
| 2018/0211562 A1 | 7/2018 | Rios | |
| 2018/0333543 A1 | 11/2018 | Diaz | |
| 2018/0369481 A1 | 12/2018 | Pedersen | |
| 2019/0009029 A1 | 1/2019 | Fabricius | |
| 2019/0255252 A1 | 8/2019 | Gentz | |

FOREIGN PATENT DOCUMENTS

| | | |
|---|---|---|
| EP | 2301599 A1 | 3/2011 |
| EP | 3381494 A1 | 10/2018 |
| KR | 200450065 Y1 | 9/2010 |
| KR | 200451044 Y1 | 11/2010 |
| WO | 2006045215 A1 | 5/2006 |
| WO | 2014029683 A1 | 2/2014 |
| WO | 2017070391 A2 | 4/2017 |
| WO | 2018125887 A2 | 7/2018 |
| WO | 2018138051 A1 | 8/2018 |

* cited by examiner

INJECTION DEVICE

CROSS REFERENCE TO RELATED APPLICATIONS

This application is a continuation of U.S. patent application Ser. No. 16/580,075, filed Sep. 24, 2019, and published as U.S. Patent App. Pub. No. 2020/0093994 on Mar. 26, 2020, which claims priority to Great Britain Patent App. No. 1815552.3, filed Sep. 24, 2018, the disclosures of which are hereby incorporated by reference herein.

FIELD OF THE INVENTION

This disclosure relates to the field of injection devices for delivering medicament, in particular to plunger rods for injection devices, for example plunger rods for prefilled syringes.

BACKGROUND OF THE INVENTION

A well-known injection device is a syringe for delivery of medicament via a needle. A typical syringe includes a barrel containing a reservoir of medicament which may be a prefilled cartridge of medicament. The barrel has a needle at the distal end thereof in fluid communication with the medicament. The proximal end of the reservoir of medicament is closed and sealed by a stopper or piston which can be made to move axially forwards in order to deliver medicament through the needle from the reservoir. The stopper is made to move axially by a user applying an axial force to a plunger rod which is locatable in the barrel and coupled to the stopper.

In some syringes, the stopper is an integral part of the plunger rod. In other syringes, the plunger rod and stopper are separate components attached together. This is typically achieved by providing a screw thread on the distal end of the plunger rod which can be engaged in a corresponding screw thread on the stopper. The stopper generally has a small screw-threaded hole on the proximal side thereof, into which the distal end of the plunger rod can be screwed. An example of this type of screw-threaded plunger rod is illustrated in U.S. Pat. No. 6,129,712 A. Another method of attaching the plunger rod and stopper together is referred to in U.S. Pat. No. 4,252,118 A involving a reduced tip on the plunger rod terminating in a flanged head. The flanged head and reduced tip are adapted to be received in an accommodating recess in the rubber stopper by snapping into place in conventional fashion.

Prefilled syringes are typically supplied fitted with a plunger rod already screwed into the thread present in the stopper.

A disadvantage of known plunger rods is that, in a disposable syringe intended for single-use, it may be possible for the user to pull back on the plunger rod after delivery of the medicament, potentially to refill the syringe in an unsafe manner. U.S. Pat. No. 4,252,118 A addresses this problem by providing a non-reusable prefilled syringe assembly in which the rod can be quickly and easily detached from the stopper after single use and disposed of, thereby facilitating the provision of a single use syringe assembly. The plunger rod is destroyed after easy removal from the stopper and there would be no rod available for reuse purposes.

A further disadvantage occurs in applications for subcutaneous delivery. It is common practice for intramuscular injections for the user to pull back on the plunger rod to check whether the needle is in a blood vessel before delivering the dose of medicament. This is referred to as "the vein test" in U.S. Pat. No. 4,252,118 A. The "vein test" is unnecessary for subcutaneous delivery. Indeed, some formulations of medicament for subcutaneous delivery may be compromised if the plunger rod is pulled back before injecting. For example, some formulations crystalize on contact with water and may solidify in the needle if the plunger rod is pulled back.

SUMMARY OF THE INVENTION

In accordance with an aspect of the present invention there is provided an injection device, including a barrel having a medicament reservoir therein capable of fluid communication with a needle assembly at a distal end thereof and sealed at a proximal end thereof with a stopper. The injection device further includes a plunger rod having a distal rod end which is couplable with said stopper, wherein, when the plunger rod is coupled to the stopper, forward axial movement of the plunger rod causes forward axial movement of the stopper coupled thereto into the medicament reservoir in order to expel medicament through the needle assembly. Further, the plunger rod can be decoupled from the stopper by applying a rearward axial force on the plunger rod, said rearward axial decoupling force being less than a rearward axial force required to move the stopper rearwardly with respect to the barrel.

It is not possible to perform the above-described "vein test" with the injection device described above as the user is completely prevented from pulling back on the stopper. Any rearward axial force on the plunger rod causes the plunger rod to decouple from the stopper because the rearward axial decoupling force is less than the force required to move the stopper rearwardly with respect to the barrel. Preventing the user from pulling back on the stopper also has the advantage of preventing the user from undesirably refilling a single-use syringe for attempted reuse.

In some embodiments, said distal rod end is coupled with a proximally-facing screw-threaded recess in the stopper.

In some embodiments, said distal rod end includes a spherical end portion engageable with said screw-threaded recess in the stopper. Alternatively, said distal rod end includes a ribbed portion having one or more radially extending ribs engageable with said screw-threaded recess in the stopper.

In some embodiments, the coupling between said distal rod end and said screw-threaded recess in the stopper is a snap-fit. Alternatively, the coupling between said distal rod end and said screw-threaded recess in the stopper is a friction-fit.

In some embodiments, said rearward axial decoupling force is less than 10N, for example 2N.

In some embodiments, when the plunger rod is coupled to the stopper, said distal rod end remains coupled to said stopper when the injection device is held in a plunger-down orientation.

In some embodiments, said distal rod end is couplable with said stopper by abutment therewith. Said distal rod end may include a distally-facing stopper-engaging surface to facilitate said abutment with the stopper.

In some embodiments, said plunger rod includes a barrel-engaging element which extends radially from said plunger rod to resiliently engage an internal surface of said barrel. Said barrel-engaging element may include one or more airflow passages to permit airflow around the barrel-engaging element.

The barrel-engaging element may include an annular ratchet element wherein a forward axial force required to push the plunger rod into the barrel is less than a rearward axial force required to pull the plunger rod out of the barrel. In some embodiments, the barrel-engaging element include a plurality of said annular ratchet elements arranged axially along said plunger rod.

In some embodiments, the distal rod end is couplable with said stopper via a magnetic interface therebetween. The magnetic interface may include a magnet at the distal rod end and a ferromagnetic material insert on said stopper. Alternatively, the magnetic interface may include a magnet on said stopper and a ferromagnetic material insert on said distal rod end.

In some embodiments, said ferromagnetic material insert is externally threaded and configured to be engaged with the internal screw thread of a standard prefilled syringe or standard prefilled cartridge stopper.

In some embodiments, the injection device further includes electrically conductive elements in each of said distal rod end and said stopper which, when the distal rod end is coupled with said stopper, complete an electrical circuit. Said electrically conductive elements may include said magnetic interface.

In some embodiments, said electrical circuit is used to power on the injection device when the distal rod end is coupled with said stopper. The electrical circuit may be used to provide the user with visual, audible or tactile feedback as to the readiness of the injection device for use.

In some embodiments, the plunger rod includes a proximal head and wherein the proximal head includes a 360° LED visible to the user, in use, to provide said visual feedback.

In some embodiments, the plunger rod is reusable.

In some embodiments, the medicament reservoir is a standard prefilled cartridge and wherein said stopper is the stopper of said standard prefilled cartridge.

The injection device may further include injection monitoring circuitry. The injection monitoring circuitry includes an input to receive force measurement data from a force sensor, the force measurement data comprising a plurality of timestamped force measurements of force applied by a user to the injection device when an injection is administered to an injection site. The injection monitoring circuitry further includes processing circuitry configured to determine from the force measurement data when an end of injection has been reached, the end of injection corresponding to the plunger rod having reached an end position in a distal portion of the barrel of the syringe during administration of the injection by the user.

According to another aspect of the invention there is provided a plunger rod for use in an injection device as described in any of the preceding paragraphs, wherein the plunger rod has a distal rod end which is couplable with the stopper of the injection device, wherein the plunger rod can be decoupled from the stopper by applying a rearward axial force on the plunger rod, said rearward axial decoupling force being less than a rearward axial force required to move the stopper rearwardly with respect to the barrel of the injection device.

In some embodiments, at least a portion of the injection monitoring circuitry is provided in a proximal head of the plunger rod.

Further aspects, features and advantages of the present invention will be apparent from the following description of preferred embodiments with reference to the accompanying drawings.

DETAILED DESCRIPTION OF THE INVENTION

Figure 1:
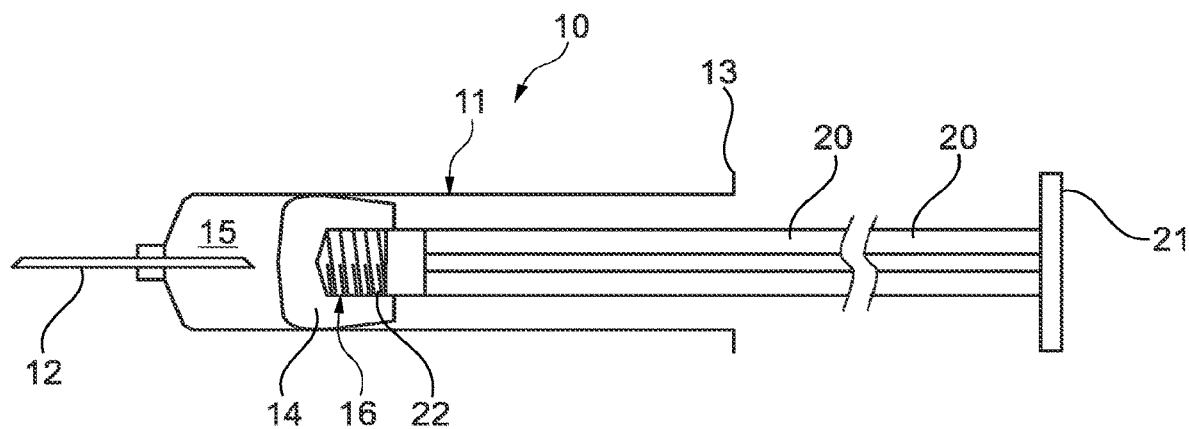
FIG. 1 is a schematic view of a prior art injection device showing a screw-threaded plunger rod connected to a screw-threaded stopper.

In the present disclosure, the following terms may be understood in view of the below explanations:

The term "injection device" may refer to a device intended for the injection of a medicament to the body and includes devices configured for various delivery methods, such as intradermal, subcutaneous, intramuscular, intravenous, intraosseous, intraperitoneal, intrathecal, epidural, intracardiac, intraarticular, intracavernous, and intravitreal, which may include via a cannula, catheter or similar device. The term includes syringes of all types, devices that contain said syringes such as auto-injectors, pen-injectors, patch injectors and other similar devices.

The term "user" may refer to a medical practitioner, end user or other user associated therewith.

The terms "coupled" or "coupling" may refer to any connection between components (not necessarily a direct connection; there may be intermediate components therebetween i.e. an indirect connection) that enables a force to be transmitted between the components. The connection may be temporary and the components need not be physically or mechanically attached to one another.

The term "plunger rod" may refer to a plunger rod, piston rod or plunger stem which can be coupled to a stopper or piston that is axially moveable in a barrel to expel medicament from the injection device. The plunger rod may incorporate a proximal head.

The terms "forward" or "forwards" or "distal" may refer to a direction towards the end of the injection device from which medicament is expelled.

The terms "backward", "backwards", "rearwards" or "rearwardly" or "proximal" may refer to a direction away from the end of the injection device from which medicament is expelled.

The term "plunger-down orientation" may mean an orientation in which the injection device is held with its distal end, i.e. the needle end, pointing upwards and its proximal end, i.e. the plunger end, pointing downwards.

The term "medicament" may include a substance in liquid or gas form. The medicament may be selected from the group of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying antirheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

When referring to the injection device, the term "containing the medicament", may refer to the medicament being contained within a suitable medicament container, such as a prefilled syringe or cartridge, within the injection device.

The term "friction fit" may include any type of interference fit or press fit wherein a fastening between components is achieved by friction when the components are pressed together.

The term "snap fit" may include any type of fastening between components achieved by pushing together interlocking parts of the components, including push to connect compression fittings.

The term "circuitry" may include general purpose processing circuitry configured by program code to perform specified processing functions. The circuitry may also be configured by modification to the processing hardware. Configuration of the circuitry to perform a specified function may be entirely in hardware, entirely in software or using a combination of hardware modification and software execution. Program instructions may be used to configure logic gates of general purpose or special-purpose processing circuitry to perform a processing function. Circuitry may be implemented, for example, as a hardware circuit including custom Very Large Scale Integrated, VLSI, circuits or gate arrays, off-the-shelf semiconductors such as logic chips, transistors, or other discrete components. Circuitry may also be implemented in programmable hardware devices such as Field Programmable Gate Arrays, FPGA.

FIG. 1 is included to show the basic and well-understood construction of a typical syringe 10. An elongate and generally cylindrical barrel 11 is provided with means for receiving a needle 12 or needle assembly at a distal end thereof. The proximal end of the barrel 11 includes a radially-extending finger flange 13. Medicament is contained within a reservoir 15 which may be a cartridge in the case of a prefilled syringe.

A resilient stopper 14 is located within the barrel 11, sealing the proximal end of the reservoir 15. In a prefilled syringe, the stopper 14 is standard in nature and is provided with a screw-threaded recess on its proximally-facing side for receiving the end of a plunger rod (described below).

A plunger rod 20 is located at least partially in the barrel 11. The proximal end of the plunger rod 20 has a proximal head 21 and the distal rod end 22 is provided with a screw-thread which can engage with the corresponding screw-thread in the stopper 14. The syringe may be provided to the user ready to use, with a plunger rod 20 already screwed into the stopper 14. Alternatively, the user may have to screw the plunger rod 20 into position before a dose of medicament can be delivered.

When it is desired to deliver a dose of medicament, the user presses the proximal head 21, pushing the plunger rod 20 axially into the barrel 11. This pushes the stopper 14 into the reservoir 15, causing medicament to be delivered from the needle.

Description of First Embodiment

Figures 2A, 2B:
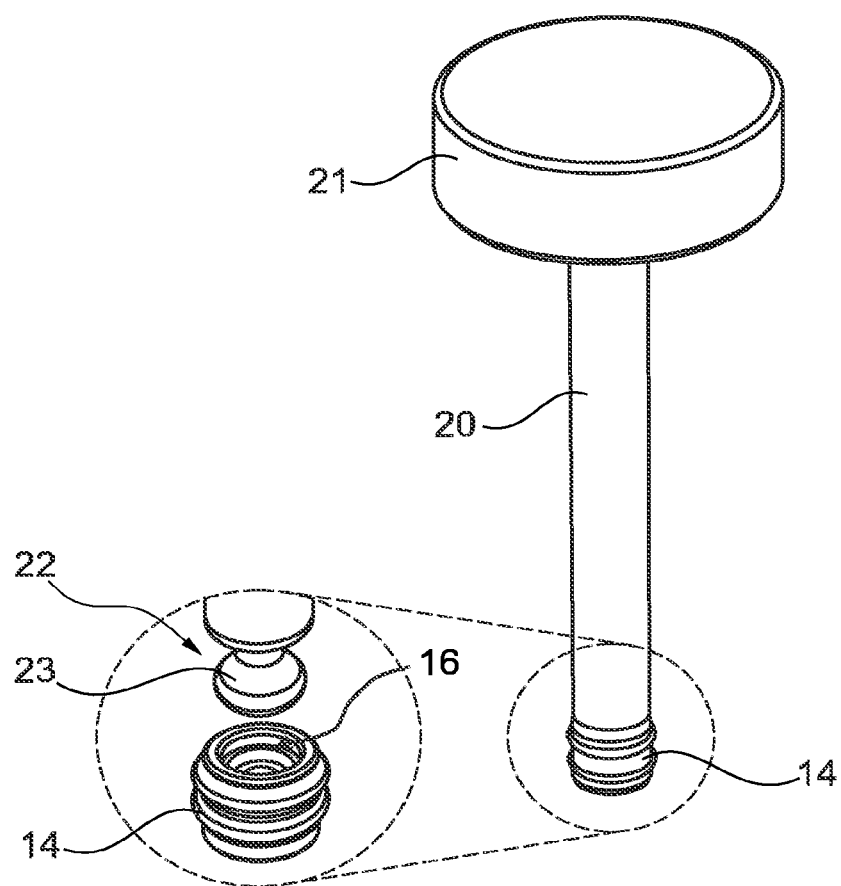
FIG. 2A shows the distal plunger rod end and a stopper of an injection device in accordance with an embodiment of the present invention.
FIG. 2B shows the distal rod end of FIG. 2A coupled with the stopper.

A non-limiting embodiment of an injection device according to the present invention is illustrated in FIGS. 2A and 2B.

FIGS. 2A and 2B show the distal plunger rod end 22 and a stopper 14 of an injection device in accordance with an embodiment of the present invention. The proximal end of the plunger rod 20 has a proximal head 21 and the distal rod end 22 is provided with a spherical portion 23, as illustrated in FIG. 2A. The stopper 14 is a standard prefilled syringe stopper having the screw-threaded recess 16 mentioned above. The spherical portion 23 may alternatively be an oblate sphere or a more irregular rounded three-dimensional shape to cooperate with the stopper 14 by engaging with it to allow the stopper 14 to be moved axially towards the distal end of the syringe barrel 104.

The spherical portion 23 of the distal rod end 22 has a maximum diameter designed to enable it to be engaged with the screw-threaded recess 16 by a simple friction-fit or snap-fit. The resilience of the stopper material facilitates this. Instead of the screw-threads of the recess 16 serving their usual function (receiving a screw-threaded distal rod end), the screw-threads serve as relatively small, elastic or resilient ribs which can engage the incoming spherical portion 23, helping to lightly retain it within the recess 16.

When it is desired to attach the plunger rod 20 to the stopper 14, the user simply inserts the distal rod end 22 into the proximal end of the barrel 11 and pushes axially forwards until the spherical portion 23 is engaged in the recess 16. This is much quicker and simpler than the prior art technique of rotating a screw-threaded rod into the screw-threaded recess 16.

When it is desired to deliver a dose of medicament, the user presses on the proximal head 21 and the forward axial force is transmitted through the spherical portion 23 of the distal rod end 22 to the stopper 14 which, in turn, moves axially forwards to expel medicament from the reservoir 15.

The coupling between the distal rod end 22 and the stopper 14 need only be sufficient to enable transmission of the forward axial force. The components need not be physically connected together. The screw-threads of the recess 16 mentioned above, although they may assist in lightly retaining the spherical portion 23 of the distal rod end 22, do not do so with any significant force and the plunger rod 20 can be easily decoupled from the stopper 14 by applying a rearward axial force to the plunger rod 20.

Description of Second Embodiment

Figures 3A, 3B:
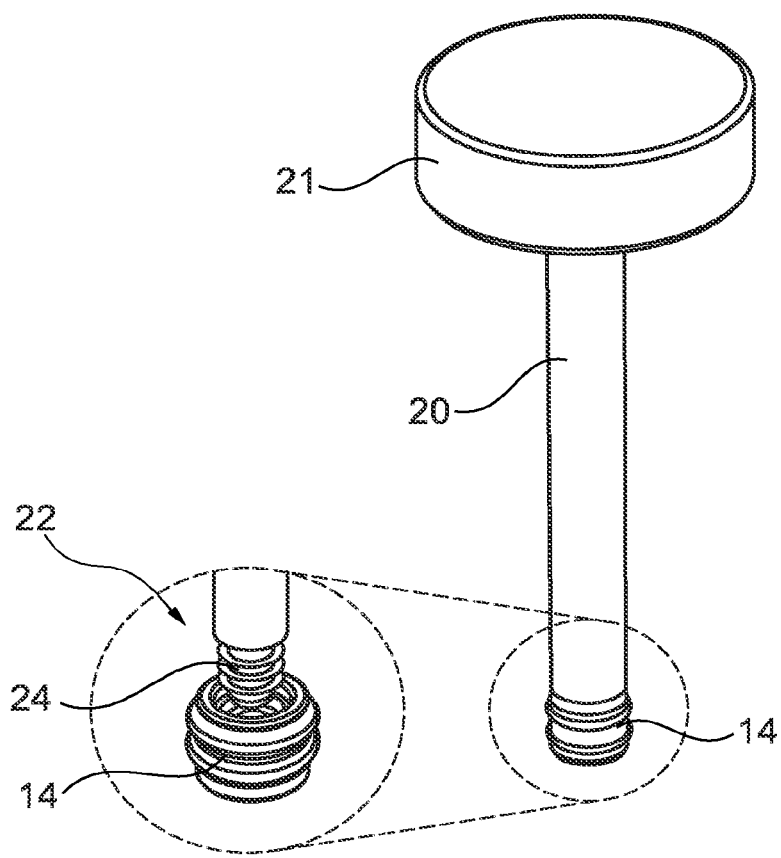
FIG. 3A shows the distal plunger rod end and a stopper of an injection device in accordance with another embodiment of the present invention.
FIG. 3B shows the distal rod end of FIG. 3A coupled with the stopper.

A further, non-limiting, embodiment of an injection device according to the present invention is illustrated in FIGS. 3A and 3B.

The proximal end of the plunger rod 20 has a proximal head 21 and the distal rod end 22 is provided with a ribbed portion 24, as illustrated in FIG. 3A. The ribbed portion 24 includes one or more radially-extending annular ribs mounted on a narrowed diameter portion of the distal rod end 22. The ribs may or may not be resilient.

The stopper 14 is a standard prefilled syringe stopper having the screw-threaded recess 16 mentioned above.

The ribbed portion 24 of the distal rod end 22 has a maximum diameter designed to enable it to be engaged with the screw-threaded recess 16 by a simple friction-fit or snap-fit. The resilience of the stopper material (and potentially the ribs) facilitates this. Instead of the screw-threads of the recess 16 serving their usual function (receiving a screw-threaded distal rod end), the screw-threads serve as relatively small, elastic or resilient ribs which can engage the incoming ribbed portion 24, helping to lightly retain it within the recess 16.

When it is desired to attach the plunger rod 20 to the stopper 14, the user simply inserts the distal rod end 22 into the proximal end of the barrel 11 and pushes axially forwards until the ribbed portion 24 is engaged in the recess 16. This is much quicker and simpler than the prior art technique of rotating a screw-threaded rod into the screw-threaded recess 16.

When it is desired to deliver a dose of medicament, the user presses on the proximal head 21 and the forward axial force is transmitted through the ribbed portion 24 of the distal rod end 22 to the stopper 14 which, in turn, moves axially forwards to expel medicament from the reservoir 15.

The coupling between the distal rod end 22 and the stopper 14 need only be sufficient to enable transmission of the forward axial force. The components need not be physically connected together. The screw-threads of the recess 16 mentioned above, although they may assist in lightly retaining the ribbed portion 24 of the distal rod end 22, do not do so with any significant force and the plunger rod 20 can be easily decoupled from the stopper 14 by applying a rearward axial force to the plunger rod 20.

It is not possible to perform the above-described "vein test" with the plunger rod 20 of FIG. 2A or 3A as the user is completely prevented from pulling back on the stopper 14. Rearward axial movement of the plunger rod 20 causes the spherical portion 23 or ribbed portion 24 of the distal rod end 22 to uncouple from the recess 16 because the force required to uncouple the distal rod end 22 from the recess 16 is substantially less than the force required to move the stopper 14 rearwardly with respect to the barrel 11. Preventing the user from pulling back on the stopper 14 also has the advantage of preventing the user from undesirably refilling a single-use syringe for attempted reuse.

Although the force required to uncouple the distal rod end 22 is very low, perhaps only 1-2N, the distal rod end 22 is retained in the stopper 14 with enough force to prevent the plunger rod 20 from simply falling out of the barrel 11 in the event the user holds the injection device in a "plunger-down" position i.e. with the needle pointing upwards.

Description of Third Embodiment

Figure 4:
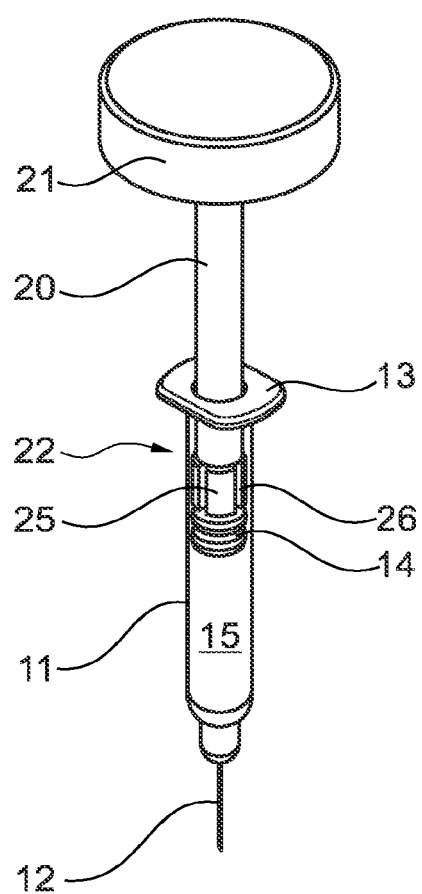
FIG. 4 shows an injection device in accordance with another embodiment of the invention.
Figure 5A:
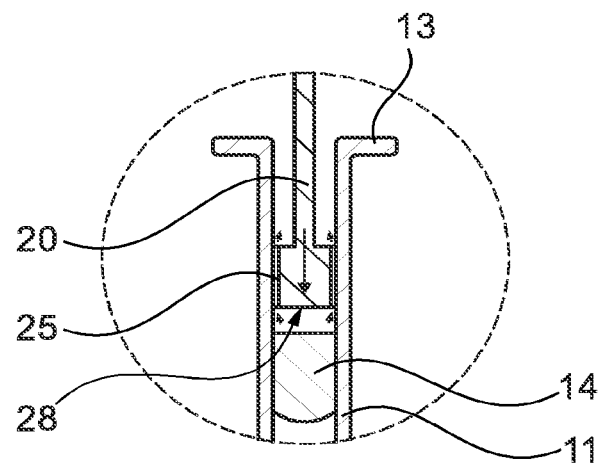
FIG. 5A shows forward axial movement of the distal rod end of FIG. 4.
Figure 5B:
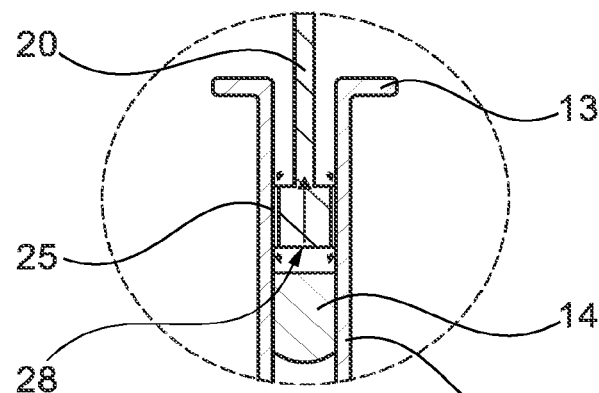
FIG. 5B shows rearward axial movement of the distal rod end of FIG. 4.

A further, non-limiting, embodiment of an injection device according to the present invention is illustrated in FIGS. 4, 5A and 5B.

In this embodiment, instead of coupling the distal rod end 22 with a recess in the stopper 14, the distal rod end 22 is coupled to the stopper by simply abutting the distal rod end 22 against the stopper 14 to enable forward axial force to be transmitted.

The distal rod end 22 has a distally-facing stopper-engaging surface 28 which can abut the proximally-facing side of the stopper 14. The lack of any physical connection between the distal rod end 22 and the stopper 14 means that it is impossible for the user to pull back on the stopper 14. Any rearward axial movement of the plunger rod 20 causes the distal rod end 22 to uncouple and separate from the stopper 14.

The plunger rod 20 is provided with a barrel-engaging element 25, best shown in FIG. 4. In the FIG. 4 embodiment, the barrel-engaging element 25 includes several, preferably equispaced, ribs 26 with airflow passages therebetween. The ribs 26 extend radially-outwardly from the distal rod end 22 to engage with an internal surface of the barrel 11. The ribs 26 may be resilient.

When it is desired to attach the plunger rod 20 to the stopper 14, the user simply inserts the barrel-engaging element 25 into the proximal end of the barrel 11 and pushes axially forwards to overcome the resistance of the ribs 26 interacting with the internal surface of the barrel 11 until the stopper-engaging surface 28 abuts the stopper 14. This is much quicker and simpler than the prior art technique of rotating screw a screw-threaded rod into the screw-threaded recess 16. As the plunger rod 20 is pushed axially forwards (as represented in FIG. 5A) the airflow passages allow air to flow in the direction indicated by the small arrows in FIG. 5A. This prevents a build-up of pressure immediately behind the stopper 14 which otherwise might cause the stopper 14 to move axially forward, potentially delivering some medicament early and in an uncontrolled manner.

When it is desired to deliver a dose of medicament, the user presses on the proximal head 21 of the plunger rod 20 and the forward axial force is transmitted through the abutment of stopper-engaging surface 28 and stopper 14 which, in turn, moves the stopper 14 axially forwards to expel medicament from the reservoir 15.

When it is desired to remove the plunger rod 20 from the injection device, the user pulls axially rearwardly on the proximal head 21 to overcome the resistance of the ribs 26 interacting with the internal surface of the barrel 11. The airflow passages permit airflow past the barrel-engaging element 25, as indicated by the small arrows in FIG. 5B.

The resistance of the ribs 26 interacting with the internal surface of the barrel 11, when the plunger rod 20 is moved axially in either direction is relatively low and is easily overcome. However, the interaction of the ribs 26 with the internal surface of the barrel 11 is sufficient to prevent the plunger rod 20 from simply falling out of the barrel 11 in the event the user holds the injection device in a "plunger-down" position i.e. with the needle pointing upwards.

Description of Fourth Embodiment

Figure 6:
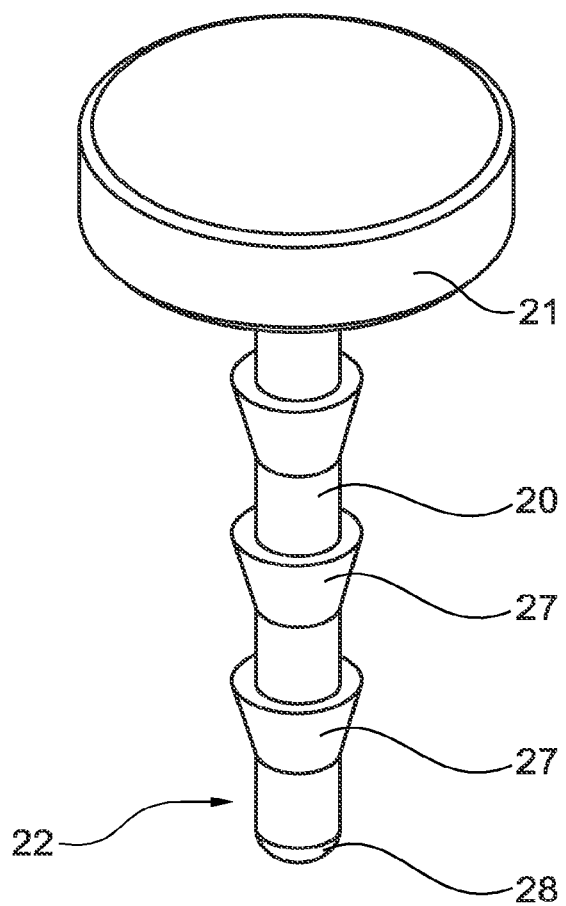
FIG. 6 shows a plunger rod in accordance with another embodiment of the invention.
Figure 7:
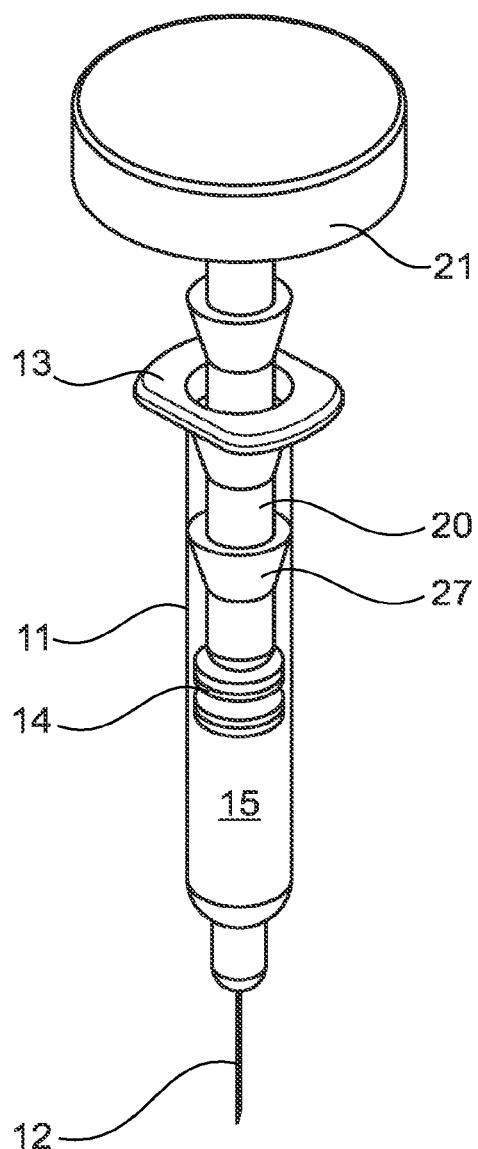
FIG. 7 shows the plunger rod of FIG. 6 in the barrel of the injection device.

A further, non-limiting, embodiment of an injection device according to the present invention is illustrated in FIGS. 6 and 7.

As in the third example embodiment above, in this fourth example embodiment instead of coupling the distal rod end 22 with a recess in the stopper 14, the distal rod end 22 is coupled to the stopper by simply abutting the distal rod end 22 against the stopper 14 to enable forward axial force to be transmitted.

The distal rod end 22 has a distally-facing stopper-engaging surface 28 which can couple with, by abutting, the proximally-facing side of the stopper 14. The lack of any physical connection between the distal rod end 22 and the stopper 14 means that it is impossible for the user to pull back on the stopper 14. Any rearward axial movement of the plunger rod 20 causes the distal rod end 22 to uncouple and separate from the stopper 14. In this embodiment, the stopper-engaging surface 28 is curved so that it can at least partially enter the recess 16 in the stopper 14.

The plunger rod 20 is provided with a barrel-engaging element in the form of an annular ratchet element 27. Several ratchet elements 27 are provided, axially-spaced along the plunger rod 20. The ratchet elements 27 extend radially-outwardly from the plunger rod 20 to engage with an internal surface of the barrel 11. The ratchet elements 27 may be resilient.

The ratchet elements 27 are generally cone-shaped such that the forward axial force required to overcome the resistance of the ratchet elements 27 engaging the internal surface of the barrel 11 to push the plunger rod 20 into the barrel 11 is less than the rearward axial force required to overcome the resistance of the ratchet elements 27 engaging the internal surface of the barrel 11 to pull the plunger rod 20 out of the barrel 11.

When it is desired to attach the plunger rod 20 to the stopper 14, the user simply inserts the plunger rod 20 into the proximal end of the barrel 11 and pushes axially forwards to overcome the resistance of the ratchet elements 27 interacting with the internal surface of the barrel 11 until the stopper-engaging surface 28 abuts the stopper 14, as illustrated in FIG. 7. This is much quicker and simpler than the prior art technique of rotating a screw-threaded rod into the screw-threaded recess 16.

When it is desired to deliver a dose of medicament, the user presses on the proximal head 21 of the plunger rod 20 and the forward axial force is transmitted through the abutment of stopper-engaging surface 28 and stopper 14 which, in turn, moves the stopper 14 axially forwards to expel medicament from the reservoir 15.

When it is desired to remove the plunger rod 20 from the injection device, the user pulls axially rearwardly on the proximal head 21 to overcome the resistance of the ratchet elements 27 interacting with the internal surface of the barrel 11.

The resistance of the ratchet elements 27 interacting with the internal surface of the barrel 11, when the plunger rod 20 is moved axially in either direction is relatively low (although greater in the proximal direction) and is easily overcome. However, the interaction of the ratchet elements 27 with the internal surface of the barrel 11 is sufficient to prevent the plunger rod 20 from simply falling out of the barrel 11 in the event the user holds the injection device in a "plunger-down" position i.e. with the needle pointing upwards.

It is not possible to perform the above-described "vein test" with the plunger rods 20 of the third and fourth example embodiments (FIGS. 4-7) as the user is completely prevented from pulling back on the stopper 14. Any rearward axial movement of the plunger rod 20 causes the stopper-engaging surface 28 of the distal rod end 22 to uncouple from the stopper 14 because they are not mechanically connected together and can simply separate from one another. Preventing the user from pulling back on the stopper 14 also has the advantage of preventing the user from undesirably refilling a single-use syringe for attempted reuse.

Description of a Fifth Embodiment

Figure 8:
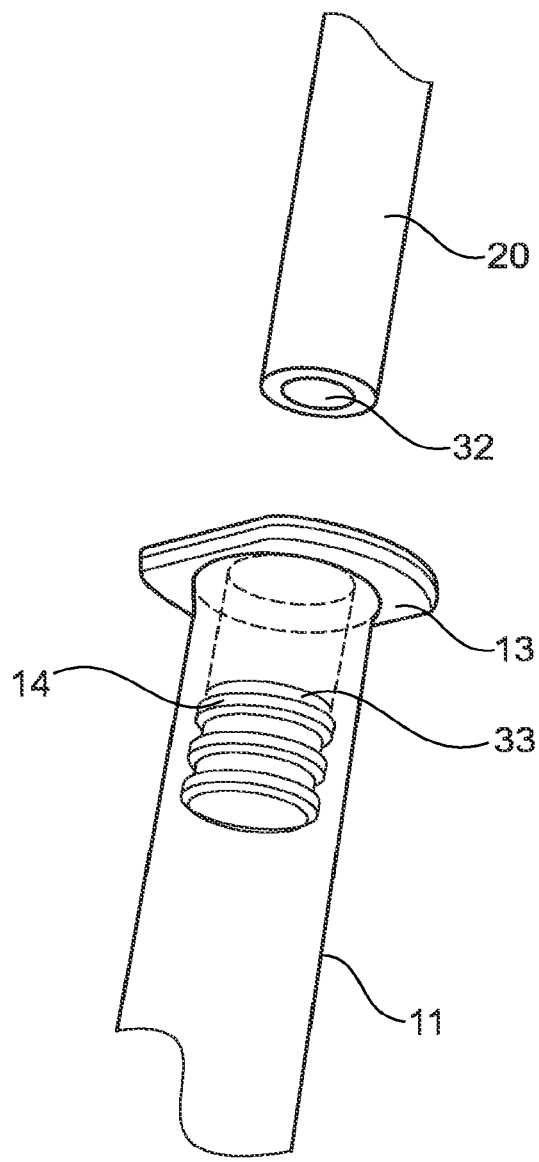
FIG. 8 shows an injection device in accordance with another embodiment of the invention.
Figure 9C:
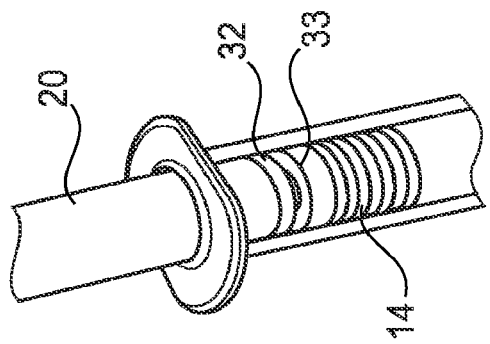
FIGS. 9A-9C show further details of the magnetic interface in the injection device of FIG. 8.
Figure 9B:
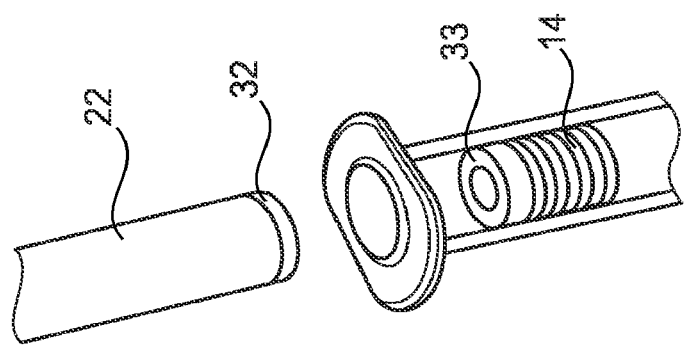
Figure 9A:
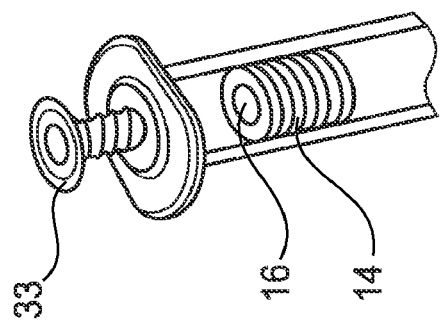
Figure 10:
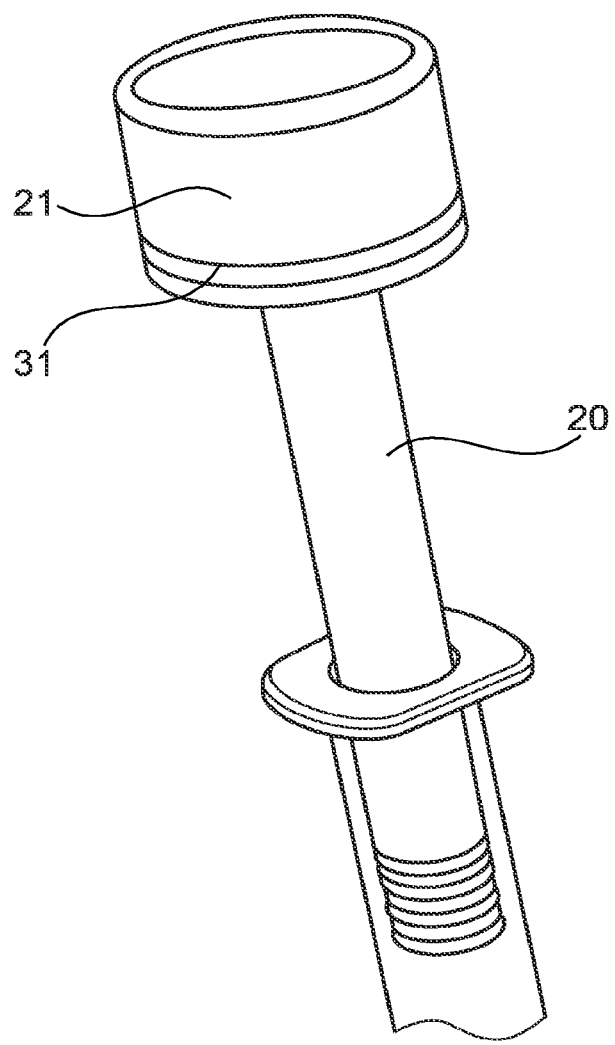
FIG. 10 shows the proximal head of the plunger of the injection device of FIG. 8.

A further, non-limiting, embodiment of an injection device according to the present invention is illustrated in FIGS. 8-10.

As in the third and fourth example embodiments above, in this fifth example embodiment, instead of coupling the distal rod end 22 with a recess in the stopper 14, the distal rod end 22 is coupled to the stopper by simply abutting the distal rod end 22 against the stopper 14 to enable forward axial force to be transmitted.

In this embodiment, the distal rod end is couplable with said stopper via a magnetic interface therebetween. As illustrated in FIG. 8, the distal rod end 22 of the plunger rod 20 is provided with a magnet 32 inserted in and flush with the plunger rod end 22. The stopper 14 is provided with a ferromagnetic material insert 33. It will be appreciated that the magnet could alternatively be provided on the stopper 14 with the ferromagnetic material on the distal rod end 22.

The stopper 14 may be a conventional stopper 14 adapted to include a magnet 32 or a ferromagnetic material insert 33. Alternatively, the distal rod end 22 may be provided with an integrally formed magnet 32 or ferromagnetic material insert 33 or be formed from a material containing suspended magnetic particles (e.g. a rubber magnet) such that it generates a magnetic field to enable coupling to a ferromagnetic material insert 33 provided on the distal rod end 22.

The magnet 32 may be a permanent magnet at room temperature. However, an electromagnet could alternatively be used. Examples of magnetic materials that may be used include iron, nickel, cobalt and steel. The strength of the magnetic field strength generated by the ferromagnetic material insert 33 and magnet 32 may be adapted according to a desired coupling force. At a minimum, the coupling force may be sufficiently strong to allow the plunger rod end 22 to engage with the stopper 14 to efficiently and effectively deliver a full dose of a medicament to an injection site. The ferromagnetic material insert 33 may conveniently provide a snap-fit or a friction fit or a screw fit to the stopper 14, which promotes easy assembly of the injection device.

FIG. 9A shows further detail of the ferromagnetic material insert 33. The insert 33 is made from a ferromagnetic metal and has an external screw thread which is suitably dimensioned that it can be screwed into the small screw-threaded recess 16 provided on the proximal side of a standard prefilled syringe stopper 14. This enables the plunger rod and magnetic interface described herein to be implemented with an otherwise entirely standard prefilled syringe.

When it is desired to attach the plunger rod 20 to the stopper 14, the user simply inserts the distal rod end 22 into the proximal end of the barrel 11 as shown in FIGS. 9B and 9C and pushes axially forwards until the magnetic interface between the magnet 32 and insert 33 causes the rod 20 and stopper 14 to be coupled to one another. This position is shown in FIG. 10.

When it is desired to deliver a dose of medicament, the user presses on the proximal head 21 of the plunger rod 20 and the forward axial force is transmitted through the distal rod end 22 to the stopper 14 which, in turn, moves axially forwards to expel medicament from the reservoir 15.

It is not possible to perform the above-described "vein test" with the plunger rod 20 of FIGS. 8-10 as the user is completely prevented from pulling back on the stopper 14. Rearward axial movement of the plunger rod 20 causes the magnetic interface between the magnet 32 and the insert 33 to be broken because the force required overcome the force maintaining the coupling (i.e. to separate the distal rod end 22 from the stopper 14) is substantially less than the force required to move the stopper 14 rearwardly with respect to the barrel 11. Preventing the user from pulling back on the stopper 14 also has the advantage of preventing the user from undesirably refilling a single-use syringe for attempted reuse.

Although the force required to uncouple the distal rod end 22 is very low, perhaps only 1-2N, the magnetic interface maintaining the coupling of the distal rod end 22 in the stopper 14 is enough to prevent the plunger rod 20 from simply falling out of the barrel 11 in the event the user holds the injection device in a "plunger-down" position i.e. with the needle pointing upwards.

Device Readiness Indicator

In any of the above-described embodiments, regardless of the nature of the coupling between the plunger rod 20 and the stopper 14, a device readiness indicator may be provided.

The injection device includes electrically conductive elements in each of the distal rod end 22 and the stopper 14 which, when the distal rod end 22 is coupled with the stopper 14, complete an electrical circuit. Completion of this circuit can be used to provide an indication to the user, in the form of visual, audible and/or tactile feedback, that the plunger rod 20 has been properly coupled to the stopper 14 and therefore the injection device is ready to use.

In the first and second example embodiments described above, the electrically conductive elements are provided on the spherical portion 23 or ribbed portion 24 of the distal rod end 22 and in the recess 16.

In the third and fourth example embodiments described above, the electrically conductive elements are provided on the distally-facing stopper-engaging surface 28 and the proximally-facing side of the stopper 14. A ferromagnetic material insert 33 may alternatively be screwed into the stopper 14.

In the fifth example embodiment described above, the electrically conductive elements include the magnet 32 and the ferromagnetic material insert 33.

Components relating to the electrical circuit and the device readiness indicator are located in the proximal head 21 of the plunger rod 20. As shown in FIG. 10, the proximal head 21 is provided with a 360° LED 31 which is readily visible to the user from all angles. The LED is illuminated when the electrical circuit is completed, indicating the device's readiness for use. The LED may illuminate in white when the device is ready for use. If the plunger rod 20 is improperly coupled, or needs replacing (for example if its planned lifetime has been exceeded), the LED may illuminate in red.

E-Health Functionality

Figure 11:
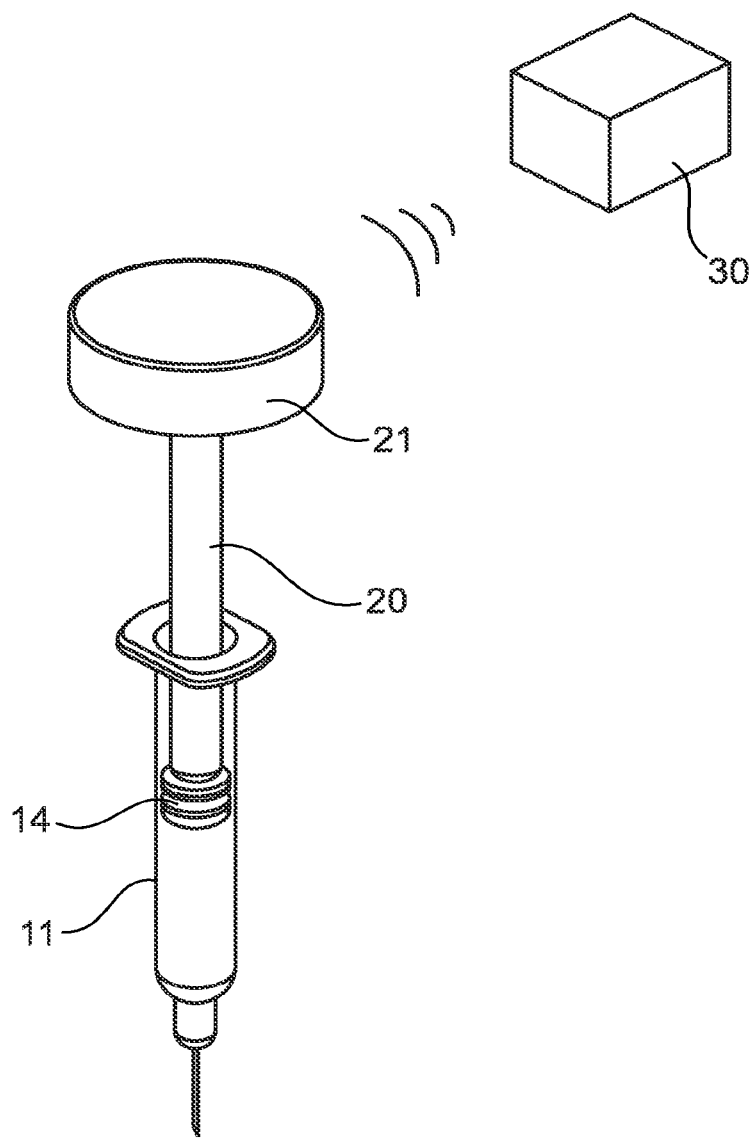
FIG. 11 shows an injection device including an e-health tool in accordance with another embodiment of the invention.

Any of the above-described embodiments can include the further optional feature of e-health functionality, as illustrated in FIG. 11. The proximal head 21 of the plunger rod 20 contains an e-health tool containing sensors and a wireless communication means for communicating with a separate e-health unit 30. The e-health tool may include injection monitoring circuitry in which timestamped force measurements are analyzed by processing circuitry to reliably determine whether or not an injection event has been successful in delivering a complete dose of a medicament. Analysis of the timestamped force measurement data may be used to provide feedback to a user of an injection device, promoting improved injection technique as might be expected from an expert user rather than an average user. Analysis of the timestamped force data may be used to discriminate between an end of injection where a complete dose has not been delivered (unsuccessful injection) and an end of injection where a complete dose has been delivered (successful injection).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. An injection device comprising:
   a stopper comprising a first conductive element;
   a barrel defining a medicament reservoir sealed at a proximal end with the stopper; and
   a plunger rod comprising a second conductive element, the plunger rod being configured to be coupled with the stopper to cause forward axial movement of the stopper to expel a medicament from the medicament reservoir, wherein coupling of the plunger rod to the stopper connects the first conductive element and the second conductive element and completes an electrical circuit.

2. The injection device of claim 1, further comprising an indicator configured to generate a visual, audible and/or tactile indication when the electrical circuit is complete.

3. The injection device of claim 2, wherein the indicator includes a light emitting diode (LED) configured to illuminate when the electrical circuit is complete.

4. The injection device of claim 3, wherein the LED extends 360° around a longitudinal axis of the injection device.

5. The injection device of claim 3, wherein the LED is positioned on a proximal portion of the plunger rod.

6. The injection device of claim 2, wherein the indicator is configured to generate a second indication when the plunger rod is improperly coupled or a part of the injection device exceeds a planned lifetime.

7. The injection device of claim 1, wherein the plunger rod is configured to be decoupled from the stopper by applying a rearward axial force to the plunger rod.

8. The injection device of claim 1, wherein a distal end of the plunger rod is configured to be coupled with a threaded recess in the stopper.

9. The injection device of claim 8, wherein the distal end of the plunger rod comprises a spherical or ribbed portion engageable with the threaded recess in the stopper.

10. The injection device of claim 1, wherein the plunger rod includes a barrel-engaging element extending radially from the plunger rod to engage an internal surface of the barrel.

11. The injection device of claim 1, wherein the first conductive element is a magnet, and the second conductive element is a magnet, and a magnetic interface between the first conductive element and the second conductive element completes the electrical circuit.

12. The injection device of claim 1, wherein the electrical circuit, when complete, is configured to power on the injection device.

13. The injection device of claim 1, further comprising a sensor configured to generate a signal indicative of a force applied to the injection device.

14. The injection device of claim 13, further comprising a processor configured to determine, from the signal, an end of injection.

15. The injection device of claim 13, wherein the signal includes force measurement data.

16. The injection device of claim 15, wherein the force measurement data is timestamped.

17. The injection device of claim 1, further comprising a wireless communication means configured to communicate with a separate unit.

18. An injection device comprising:
a stopper comprising a first conductive element;
a barrel defining a medicament reservoir sealed at a proximal end with the stopper; and
a plunger rod comprising a second conductive element, the plunger rod being configured to be coupled with the stopper to cause forward axial movement of the stopper to expel a medicament from the medicament reservoir,
wherein the first conductive element and the second conductive element complete an electrical circuit when the plunger rod is coupled to the stopper, and
wherein the plunger rod is configured to be decoupled from the stopper by applying a rearward axial force to the plunger rod.

19. The injection device of claim 18, further comprising an indicator configured to generate a visual, audible and/or tactile indication when the electrical circuit is complete.

20. The injection device of claim 19, wherein the indicator includes a light emitting diode (LED) configured to illuminate when the electrical circuit is complete.

21. An injection device comprising:
a stopper comprising a first conductive element and a threaded recess;
a barrel defining a medicament reservoir sealed at a proximal end with the stopper; and
a plunger rod comprising a second conductive element, the plunger rod being configured to be coupled with the stopper to cause forward axial movement of the stopper to expel a medicament from the medicament reservoir,
wherein the first conductive element and the second conductive element complete an electrical circuit when the plunger rod is coupled to the stopper, and a distal end of the plunger rod is configured to be coupled with the threaded recess.

22. The injection device of claim 21, wherein the distal end of the plunger rod comprises a spherical or ribbed portion engageable with the threaded recess in the stopper.

23. The injection device of claim 21, further comprising an indicator configured to generate a visual, audible and/or tactile indication when the electrical circuit is complete.

24. The injection device of claim 23, wherein the indicator includes a light emitting diode (LED) configured to illuminate when the electrical circuit is complete.

25. An injection device comprising:
a stopper comprising a first conductive element;
a barrel defining a medicament reservoir sealed at a proximal end with the stopper; and
a plunger rod comprising a second conductive element, the plunger rod being configured to be coupled with the stopper to cause forward axial movement of the stopper to expel a medicament from the medicament reservoir,
wherein the first conductive element and the second conductive element complete an electrical circuit when the plunger rod is coupled to the stopper, and
wherein the plunger rod includes a barrel-engaging element extending radially from the plunger rod to engage an internal surface of the barrel.

26. The injection device of claim 25, further comprising an indicator configured to generate a visual, audible and/or tactile indication when the electrical circuit is complete.

27. The injection device of claim 26, wherein the indicator includes a light emitting diode (LED) configured to illuminate when the electrical circuit is complete.

28. An injection device comprising:
a stopper comprising a first conductive element;
a barrel defining a medicament reservoir sealed at a proximal end with the stopper; and
a plunger rod comprising a second conductive element, the plunger rod being configured to be coupled with the stopper to cause forward axial movement of the stopper to expel a medicament from the medicament reservoir,
wherein the first conductive element and the second conductive element complete an electrical circuit when the plunger rod is coupled to the stopper, the first conductive element is a magnet, and the second conductive element is a magnet, and a magnetic interface between the first conductive element and the second conductive element completes the electrical circuit.

29. The injection device of claim 28, further comprising an indicator configured to generate a visual, audible and/or tactile indication when the electrical circuit is complete.

30. The injection device of claim 29, wherein the indicator includes a light emitting diode (LED) configured to illuminate when the electrical circuit is complete.

* * * * *